(12) United States Patent
Benjamin

(10) Patent No.: US 6,561,034 B2
(45) Date of Patent: May 13, 2003

(54) ULTRASONIC SPARSE IMAGING ARRAY

(75) Inventor: Kim C. Benjamin, Portsmouth, RI (US)

(73) Assignee: The United States of America as represented by the Secretary of the Navy, Washington, DC (US)

(*) Notice: Subject to any disclaimer, the term of this patent is extended or adjusted under 35 U.S.C. 154(b) by 44 days.

(21) Appl. No.: 09/968,396

(22) Filed: Oct. 1, 2001

(65) Prior Publication Data
US 2003/0061882 A1 Apr. 3, 2003

(51) Int. Cl.⁷ .............................................. H04R 17/00
(52) U.S. Cl. ............................ 73/641; 73/625; 73/628; 310/334
(58) Field of Search ........................ 73/641, 627, 628, 73/625; 310/334, 335, 336, 337

(56) References Cited

U.S. PATENT DOCUMENTS

| | | | | |
|---|---|---|---|---|
| 4,170,142 A | * | 10/1979 | Posakony et al. ............. 73/603 |
| 4,747,192 A | * | 5/1988 | Rokurota ..................... 29/25.35 |
| 5,629,906 A | * | 5/1997 | Sudol et al. ................. 367/162 |
| 5,644,085 A | * | 7/1997 | Lorraine et al. ............... 73/641 |
| 6,087,762 A | * | 7/2000 | Corbett et al. .............. 310/334 |

* cited by examiner

Primary Examiner—Helen Kwok
Assistant Examiner—Jacques Saint-Surin
(74) Attorney, Agent, or Firm—James M. Kasischke; Prithvi C. Lall; Michael F. Oglo

(57) ABSTRACT

An ultrasonic sparse imaging array includes a substrate of an acoustically absorptive material, through which extend a multiplicity of holes. Adhesive sheets, having selectively conductive regions, are fixed to a first side of the substrate, and are each disposed over a first end of one of the holes. Plano-convex shaped transducer elements, having a wide acoustic field of view, are disposed on each of the sheets, each of the sheets serving as a positive electrode and providing a mechanical and electrical connection between the substrate and a multiplicity of transducer elements. Plating is fixed to the first side of the substrate and covers each of the transducer elements and comprises a negative electrode. A conductive epoxy fills each of the holes and a power source is in electrical communication with the negative electrode.

15 Claims, 2 Drawing Sheets

ULTRASONIC SPARSE IMAGING ARRAY

STATEMENT OF GOVERNMENT INTEREST

The invention described herein may be manufactured and used by and for the Government of the United States of America for Governmental purposes without the payment of any royalties thereon or therefor.

CROSS REFERENCE TO OTHER PATENT APPLICATIONS

Not applicable.

BACKGROUND OF THE INVENTION

1. Field of the Invention

The invention relates to a sparse imaging array and is directed more particularly to such an array for underwater use and which requires fewer transducer elements and provides a wider area of focusing than prior art arrays.

2. Description of the Prior Art

Two dimensional arrays of underwater acoustic transducers are known. Such arrays are made by providing relatively large monolithic plates of piezo-ceramic transducer material. The plates are then cut along a series of parallel lines extending in a selected direction, and then cut along a series of parallel lines normal to the aforementioned lines, to provide a multitude of small square or rectangular block elements. A selected viscoelastic material is packed into the cut-away areas to decouple the block elements from each other.

Selected ones of the block transducer elements are then wired for operation. The remaining elements provide no benefit. Typically, only about 1%, or less, of the transducer elements are selected for wiring. In a known array, about 250,000 block elements are produced by the above-described technique, known as "dice and fill". About 1700 of the formed elements are then wired to become active elements. There is a need for an array in which such waste of materials is avoided and related costs are reduced.

Further, it is beneficial to place the active elements in positions selected with precision. However, given that the active elements of the above-described known array necessarily reside in areas defined by criss-crossing lines, the active element which is closest to the desired location is used in practice. In short, the active elements are located approximately where wanted, but not usually precisely where wanted. There is a need for an array in which the active elements are placed precisely where wanted.

Still further, the spatial response of each rectangular block element is perturbed by non-resonant lateral waves traveling in the plane of the array. Such waves occur at a critical angle based on the relative sound speeds of the array material and the surrounding fluid, typically sea water. Passing through the piezo ceramic element, such lateral waves cause an out of phase voltage with respect to a desired mode voltage and essentially limit the element beam width. There is a need for an array with improved element beamwidth.

SUMMARY OF THE INVENTION

An object of the invention is, therefore, to provide an ultrasonic sparse imaging array for underwater use, the array including a selected number of active transducer elements with no inactive transducer elements.

A further object of the invention is to provide such an array in which each transducer element is located precisely where desired on a substrate.

A still further object of the invention is to provide such an array having elements which provide a wider beam width to provide the array with a larger field of view.

A still further object of the invention is to provide a low cost method for making an ultrasonic sparse imaging array having the attributes noted immediately above.

With the above and other objects in view, a feature of the present invention is the provision of an ultrasonic sparse imaging array comprising a backing substrate of highly acoustically absorptive material, a multiplicity of holes extending through the substrate, a multiplicity of adhesive sheets having selectively conductive regions, the sheets each being fixed to a first side of the backing substrate and disposed over a first end of one of the holes, to provide a mechanical and electrical connection between the substrate and a multiplicity of transducer elements within the array. Plano-convex shaped transducer elements, each having a wide acoustic beamwidth, are respectively disposed on each of the sheets. Each of the sheets constitutes a positive electrode. A plating is fixed to the first side of the substrate, covering each of the transducer elements and constitutes a negative electrode. A conductive pin is disposed in each of the holes, the pins each being provided with an annular disc portion which closes second ends of the holes. A conductive epoxy fills each of the holes between the pin disc and the sheet. A power source is provided and is in electrical communication with the plating.

In accordance with a further feature of the invention, there is provided a method for making an ultrasonic sparse imaging array, the method comprising the steps of providing a substrate of highly absorptive material, drilling a multiplicity of holes through the substrate in a selected pattern, injecting conductive epoxy into the holes, inserting conductive pins, one each, into the holes, the pins each having an annular disc portion which is brought into engagement with the substrate undersurface to close off undersurface ends of the holes, removing epoxy overflowed from the holes from an undersurface and an upper surface of the substrate, fixing a sheet of dry film adhesive with selectively conductive regions, and comprising a positive electrode, on the upper surface of the substrate, and fixing a generally plano-convex shaped transducer element on each of the sheets, disposing a plating on the upper surface of the substrate, the plating covering the transducer elements and comprising a negative electrode, and providing connections on the plating for placing the plating in electrical communication with a power source.

The above and other features of the invention, including various novel details of construction and combinations of parts and method steps, will now be more particularly described with reference to the accompanying drawings and pointed out in the claims. It will be understood that the particular device and method embodying the invention are shown by way of illustration only and not as limitations of the invention. The principles and features of this invention may be employed in various and numerous embodiments without departing from the scope of the invention.

BRIEF DESCRIPTION OF THE DRAWINGS

Reference is made to the accompanying drawings in which is shown an illustrative embodiment of the invention, from which its novel features and advantages will be apparent, wherein corresponding reference characters indicate corresponding parts throughout the several views of the drawings and wherein.

DESCRIPTION OF THE PREFERRED EMBODIMENT

Figure 1:
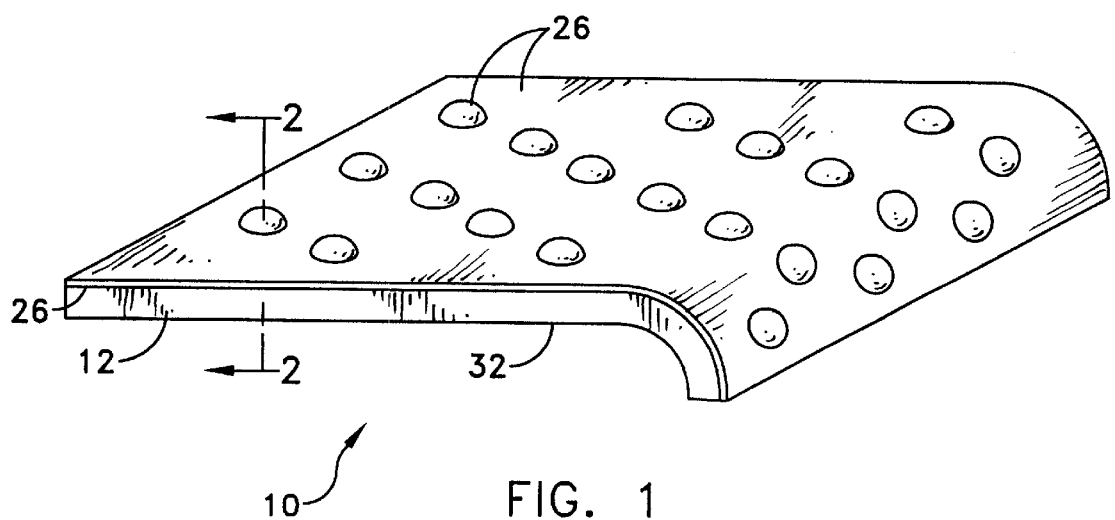
FIG. 1 is a perspective view of one form of an array illustrative of an embodiment of the invention.
Figure 2:
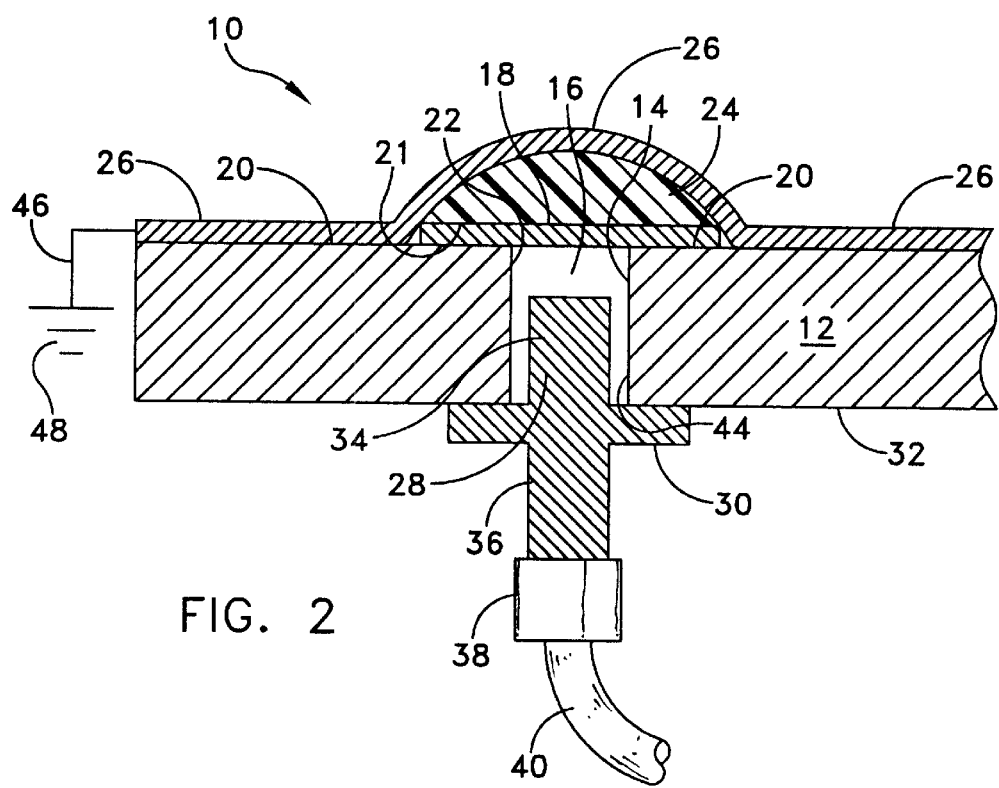
FIG. 2 is a sectional view taken along line 2—2 of FIG. 1.

Referring to FIG. 1, it will be seen that the illustrative array 10 includes a substrate, or array backing, 12 in a sheet form. The substrate 12 preferably is of a material which is highly absorptive at ultrasonic frequencies, such as tungsten-epoxy composite. The substrate can be planar, or curved in one or two directions. In the substrate 12 are disposed a multiplicity of holes 14 (FIG. 2) extending therethrough. The holes 14 are disposed at the precise locations where the presence of an active transducer element is deemed desirable. The holes 14 are packed with an electrically conductive epoxy 16.

Figure 3:
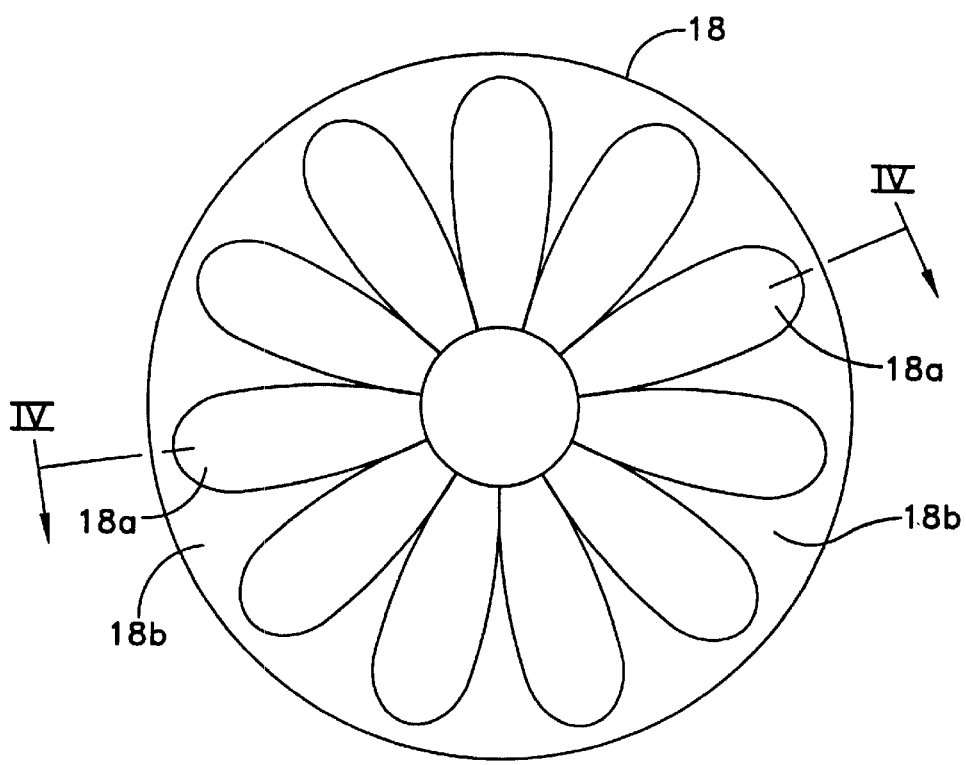
FIG. 3 is a bottom plan view of one form of a sheet portion of the transducer assembly shown in FIG. 2.

A lower positive electrode sheet 18 is disposed on an upper surface 20 of the substrate 12. The sheet 18 may be an adhesive film with selectively conductive regions 18a(FIG. 3). A plano-convex shaped transucer element 24 is placed on each of the sheets 18, with a planar surface 21 of the transducer element 24 resting on one of the sheets 18. Covering an upper end 22 of each of the holes 14, the sheet 18 provides mechanical and electrical connectivity between the substrate 12 and transducer elements 24. The plano-convex shaped transducer elements 24 preferably are comprised of a piezoelectric material, such as solid piezoceramic, piezoceramic-polymer compostie, or piezoelectric elastomer (i.e., polyviny/diflouride (PVDF)).

An upper negative electrode plating 26 is applied to the substrate upper surface 20 and over the transducer elements 24. The upper plating 26 may be of copper plating or a conductive epoxy. If copper, or other suitable metal, such as chromium, the upper plating 26 may be applied by vacuum deposition.

A conductive pin 28 is disposed in each of the holes 14. The pins 18 are of about 0.020 inch in diameter and preferably are of copper with tin plating. The pins 28 are each provided with a disc portion 30 which engages an undersurface 32 of the substrate 12. An upper portion 34 of the pin 28 is embedded in the aforementioned epoxy 16. A lower portion 36 of the pin 28 extends axially outwardly from the disc portion 30 and the substrate undersurface 32. By a connection 38 an electrically conductive wire 40 extends from a free end of the pin lower portion 36 and is, in turn, connectable to signal conditioning electronics and/or a computer with display, or the like (not shown). The connection 38 may be an interference fit socket-type (shown in FIG. 2), a wire wrap type, or simply a soldered connection. The upper negative electrode plating 26 is connected, as by wiring 46 to a power source 48.

Referring to FIG. 3, it will be seen that the sheet, or lower positive electrode, 18 may be apodised to include radially-extending electrically conductive portions 18a and non conductive portions 18b. Such a configuration, in combination with the plano-convex shaped transducers 24, serves to broaden the spatial acceptance angle and widen the field from which acoustic activity is received.

The above described array preferably is made as follows:

The substrate 12 is provided in a desired configuration which may include planar, or singly or doubly curved surfaces. The substrate 12 may be constructed in one piece or in sections. Holes 14 are drilled through the substrate 12 precisely where desired, using known Numerical Control laser drilling. The conductive epoxy 16 is then injected into the holes 14. The conductive pins 28 are then inserted into the holes 14 until the disc portions 30 of the pins 28 engage the substrate undersurface 32 to close off undersurface ends 44 of the holes 14. Any epoxy overflowing onto the substrate surfaces 20, 32 is removed to provide clean substrate surfaces 20, 32. The conductive epoxy 12 is allowed to cure.

The sheets 18, comprising the lower positive electrodes are fixed each to the upper surface 20 of the substrate 12 and over a hole 14 to close off the hole upper ends 22. The generally plano-convex shaped transducer elements 24 are then each fixed to one of the sheets 18, using known "pick and place" technology.

The plating 26, serving as the upper negative electrode, is applied to the substrate upper surface 20 so as to cover the substrate upper surface 20 and the transducer elements 24.

Figure 4:
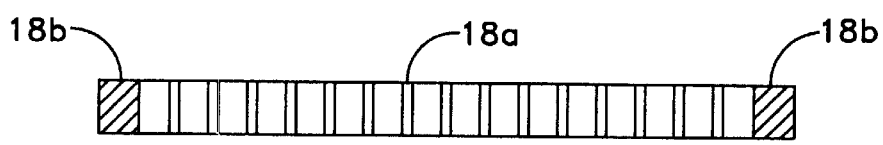
FIG. 4 is a cross section taken along line IV—IV of FIG. 3.

Finally, the plating 26 is placed in electrical communication with a power source 48 and the pins 28 are placed in electrical communication with signal enhancing electronics, and/or a computer, display, and the like, by the connection 38. FIG. 4 illustrates a cross-section of the transducer assembly shown in FIG. 3.

There is thus provided an array in which only the number of transducer elements needed are used in the apparatus. There is further provided an array in which the transducer elements are disposed precisely where they are wanted. There is still further provided an array having a wider field of view over which the array can focus, by virtue of the plano-convex shaped transducer elements and by virtue of their being placed so as not to shield one another. Finally, there is provided a method for making a sparse imaging array, that is compatible with the current "pick and place" technology, and which reduces greatly the amount of array material required, and which improves performance.

It will be understood that many additional changes in the details, materials, steps and arrangement of parts, which have been herein described and illustrated in order to explain the nature of the invention, may be made by those skilled in the art within the principles and scope of the invention as expressed in the appended claims.

What is claimed is:

1. An ultrasonic sparse imaging array comprising:
   a substrate of acoustically absorptive material;
   a multiplicity of holes extending through said substrate;
   a multiplicity of adhesive sheets, each fixed to a first side of said substrate and disposed over a first end of one of said holes, each of said sheets comprising a positive electrode;
   a generally plano-convex shaped transducer element disposed on each of said sheets;
   plating fixed to the first side of said substrate and covering each of said transducer elements and comprising a negative electrode;
   a conductive pin disposed in each of said holes, said pins each being provided with an annular protrusion which closes a second end of said holes;
   a conductive epoxy filling each of said holes between the pin disc and the sheet; and
   a power source in electrical communication with said plating.

2. The array in accordance with claim 1 wherein said substrate is of a tungsten-epoxy composite.

3. The array in accordance with claim 1 wherein each of said sheets comprises a film of patterned electrically conductive and non-conductive adhesive regions.

4. The array in accordance with claim 1 wherein said sheets comprise conductive plates.

5. The array in accordance with claim 1 wherein said transducer elements are of a material selected from a group of materials consisting of piezoelectric ceramics, piezoelectric ceramic polymer composites, and piezoelectric polymers.

6. The array in accordance with claim 5 wherein said transducer elements are fixed to said substrate by said adhesive sheets.

7. The array in accordance with claim 1 wherein said plating comprises a selected one of copper and conductive epoxy.

8. The array in accordance with claim 1 wherein said pin is of copper with tin plating.

9. The array in accordance with claim 8 wherein said pin is of a diameter of about 0.020 inch.

10. The array in accordance with claim 1 wherein said plating is adapted for electrical communication with a power source and said pin is adapted for electrical communication with signal enhancing means and computer means.

11. A method for making an ultrasonic space imaging array, the method comprising the steps of:
    providing a substrate of highly absorptive material;
    drilling a multiplicity of holes through the substrate in a selected pattern;
    injecting conductive epoxy into the holes;
    inserting conductive pins, one each, into the holes, the pins each having an annular disc portion which is brought into engagement with a substrate undersurface to close off undersurface ends of the holes;
    allowing the conductive epoxy to cure;
    removing cured epoxy overflow resulting from pin insertion from the undersurface and an upper surface of the substrate;
    fixing a sheet comprising a positive electrode on the upper surface of the substrate and over each of the holes to close off upper surface ends of the holes, the sheet comprising an adhesive film having selectively conductive regions;
    fixing a generally plano-convex shaped transducer element on to each of the sheets and over each of the holes;
    disposing a plating on the upper surface of the substrate, the plating covering the transducer elements and comprising a common negative electrode; and
    providing connections on the plating for placing the plating in electrical communication with a power source.

12. The method in accordance with claim 11 wherein the substrate comprises a sheet of material which is highly absorptive over an ultrasonic frequency range.

13. The method in accordance with claim 12 wherein fixing the positive electrode sheets to the upper surface of the substrate comprises disposing a plate of conductive material on the substrate.

14. The method in accordance with claim 12 wherein fixing the positive electrode sheets to the upper surface of the substrate sheet comprises fixing films of conductive adhesive on the substrate.

15. The method in accordance with claim 14 wherein disposing the plating on the upper surface of the substrate comprises applying the plating by vacuum deposition.

* * * * *